(12) United States Patent
Schafer

(10) Patent No.: US 9,119,602 B2
(45) Date of Patent: *Sep. 1, 2015

(54) TEMPERATURE BASED FERTILITY MONITORING SYSTEM AND RELATED METHOD

(71) Applicant: Tempsync, Menlo Park, CA (US)

(72) Inventor: Deborah Lawrence Schafer, Menlo Park, CA (US)

(73) Assignee: TEMPSYNC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/473,853

(22) Filed: Aug. 29, 2014

(65) Prior Publication Data

US 2014/0378863 A1 Dec. 25, 2014

Related U.S. Application Data

(63) Continuation of application No. 13/683,870, filed on Nov. 21, 2012, now Pat. No. 8,834,389.

(51) Int. Cl.
*A61B 10/00* (2006.01)
*A61B 5/01* (2006.01)

(52) U.S. Cl.
CPC ............... *A61B 10/0012* (2013.01); *A61B 5/01* (2013.01); *A61B 2010/0019* (2013.01)

(58) Field of Classification Search
CPC .................. A61B 5/01; A61B 10/0012; A61B 2010/0019
USPC ................... 600/549, 551, 588, 591
See application file for complete search history.

(56) References Cited

U.S. PATENT DOCUMENTS

| 4,151,831 | A | * | 5/1979 | Lester | 600/549 |
| 5,240,010 | A | * | 8/1993 | Weinmann | 600/547 |
| 6,278,999 | B1 | * | 8/2001 | Knapp | 1/1 |
| 6,419,637 | B1 | * | 7/2002 | Cheng et al. | 600/551 |
| 6,547,748 | B1 | * | 4/2003 | Shine | 600/588 |
| 7,594,889 | B2 | * | 9/2009 | St. Ores et al. | 600/301 |
| 7,771,366 | B2 | * | 8/2010 | Kirsner | 600/551 |
| 7,953,613 | B2 | * | 5/2011 | Gizewski | 705/3 |
| 8,152,735 | B2 | * | 4/2012 | Kirsner | 600/551 |
| 8,306,652 | B2 | * | 11/2012 | Bandholz et al. | 700/223 |
| 8,313,447 | B2 | * | 11/2012 | Van Leer | 600/588 |
| 8,496,597 | B2 | * | 7/2013 | James et al. | 600/551 |
| 8,834,389 | B2 | * | 9/2014 | Schafer | 600/551 |

* cited by examiner

*Primary Examiner* — Max Hindenburg
(74) *Attorney, Agent, or Firm* — Convergent Law Group LLP; Rick Batt

(57) ABSTRACT

A fertility monitoring apparatus measures body temperature and saliva or cervical fluid resistivity. The clinical device includes a sensor, processor and transmitter to wirelessly deliver information to a computerized device such as a smart phone, tablet, or laptop for further analysis and display. The computerized device is programmed with software to receive, analyze, display, and/or transmit the raw or processed information. The programmed computerized device computes fertility information of the user. A central fertility platform includes a programmed computing device, and a database of fertility information from multiple users. Input from user accounts are fed into the platform and stored in the database. Exemplary inputs include the user's age, cycle length, diagnosis of fertility, reproductive health information. The platform both provides feedback to the user and learns from the data collected to improve upon or self-modify calculations using machine learning, artificial intelligence, and data mining approaches.

20 Claims, 8 Drawing Sheets

TEMPERATURE BASED FERTILITY MONITORING SYSTEM AND RELATED METHOD

CROSS REFERENCE TO RELATED APPLICATION

This application is a Continuation of U.S. patent application Ser. No. 13/683,870, filed Nov. 21, 2012, which claims priority to provisional application No. 61/563,745, filed Nov. 25, 2011; provisional application No. 61/658,722, filed Jun. 12, 2012; and provisional application No. 61/710,880, filed Oct. 8, 2012, each of which the entirety is incorporated by reference herein.

FIELD OF THE INVENTION

This invention relates to a fertility monitoring apparatus adapted to measure biomedical information including temperature and electrical resistivity of the saliva and/or cervical fluid and to compute fertility information based on multiple inputs.

BACKGROUND OF THE INVENTION

In the United States it is estimated that over 7 million women have infertility and another 3 million women intentionally get pregnant annually. An accurate yet convenient technology to monitor fertility is therefore desired.

Temperature measurement has been found effective to assist in monitoring fertility. Daily tracking of basal body (resting) temperature is an old technique that women use to help determine when they have ovulated, as a woman's basal body temperature usually rises between 0.2 and 0.6 degrees Fahrenheit around the day of ovulation. However, tracking basal body temperature is tedious because one must remember to take her temperature the very first thing in the morning, remember the measurement, and then record it onto her paper chart or into her fertility tracking software. The frustrating and time-consuming nature of this method deters more women from using it. Furthermore, it involves some interpretation of the temperature measurements to detect the rise indicative of ovulation, and some guessing as to when the subsequent fertile window is likely to occur.

Various approaches have been developed to chart temperature for fertility and to provide an interpretation of the BBT (Basal Body Temperature) measurements.

The "Lady Comp" (manufactured by Valley-Electronics GmbH, headquartered in Murau, Germany), for example, includes a thermometer attached by an electrical cord to a stand-alone computer. An example of a thermometer for measuring the temperature in low-convection media is described in U.S. Pat. No. 4,654,623.

More inventions have been created to provide some level of interpretation of these BBT readings. U.S. patent application Ser. No. 12/766,598 (Beth Rosenshein) and Ser. No. 12/890,743 (Witold Andrew ZIARNO et al) show methods for inserting a temperature sensor with wireless capability into bodily cavities, primarily the vagina, to monitor the temperature shift seen with ovulation. Recently published US20120238900A1 (Natalie Rechberg) and US20120265032A1 (Boaz Beeri) describe a portable preprogrammed thermometer for fertility status and an ovulating sensing and analyzing system respectively.

Patent Publication No. 2007/0282218 describes a method for measuring skin temperature using two temperature sensors separated by an insulating layer. The core body temperature is derived from a calculation in the difference between the sensors.

Patent Publication No. 2011/0301493 (Shamus Husheer, Cambridge GB) describes a method involving placing one sensor next to the body and another sensor in the same incasing at another depth, parallel to the lateral direction, and calculating the core body temperature off the difference in the temperature between sensors.

Patent Publication No. 2005/0245839 to BodyMedia (John Stivoric et al) describes a non-invasive temperature monitoring device using a skin sensor for continuous wear that similarly includes a skin temperature sensor and an additional ambient temperature sensor within the same housing.

U.S. Pat. No. 7,413,544 (Robert Kerr, II) describes another system and method for collecting and transmitting medical data. In one of the described embodiments, a measuring device is a fertility thermometer. Data is acquired by a remote system. A patient views here medical profile which might include temperature readings over the fertility cycle.

The method of combining temperature and the quality of cervical mucus wherein the quality of the cervical fluid is interpreted by the individual, known as the Sympto-thermal method, and has been known since the 1930s, and is highly accurate (98%) as a contraception method when practiced perfectly. However, a problem with the method is that it is tedious and somewhat subjective to determine the quality of the cervical fluid.

Various approaches have been developed to evaluate cervical mucus. For example, U.S. Pat. No. 4,685,471 (Jennie Regas and Ranjit S. Fernando) uses cervical mucus alone to predict ovulation. This approach is utilized in the OvaCue® fertility monitor to predict ovulation in a stand-alone device (manufactured by Fairhaven Health LLC, Bellingham, Wash.). Hormonal and biochemical changes that cause a variation in the electrolyte characteristics of cervical fluid are reflected in the electrical resistivity of a woman's saliva and cervical fluid (also known as vaginal fluid or mucus). Onset of ovulation is determined as a function of a peak resistivity measurement following the onset of menstruation, which peak is followed by a nadir and subsequent sharp increase in saliva electrical resistivity measurement.

Additionally, Patent Publication Nos. 2012265032 to Ben-David et al. and 2012238900 to Rechberg describe systems for collecting and transmitting medical data and determining fertility and ovulation.

U.S. Pat. No. 5,240,010 to Weinmann describes a device for monitoring temperature and changes in the characteristics of the cervical mucus (vaginally only) for evaluation in order to determine a women's fertile window. This device evaluates the measurements and provides feedback on the degree of fertility of the subject.

Notwithstanding the above, a need still exists for an improved clinical apparatus and method that monitors a woman's fertility, and one that is accurate and convenient for her to use regularly, particularly taking measurements orally that are reflective of hormonal and temperature changes associated with ovulation, and to make the information about her fertility status conveniently available to her throughout the day.

SUMMARY OF THE INVENTION

A clinical apparatus that detects various physical parameters of a female that relates to fertility such as basal body temperature. The apparatus sends the data wirelessly to another computerized device such as a mobile phone, tablet, watch or bracelet, wireless network, or computer. The computerized device is programmed to receive and track the data, and to compute her fertility information. The associated software completes a learning system. Data points are gathered from the clinical device and manual inputs and analyzed over time to predict and analyze fertility related information, including but not limited to detecting the fertile window, and predicting the onset of menses. Additional features of the device may include an alarm, a display, battery charge status indicator, clock, etc. In one embodiment, data is tracked over time and an ovulation window is estimated.

The configuration of the clinical apparatus may vary. In one embodiment, the clinical apparatus is a thermometer-like device. It may be shaped for use orally, vaginally, or on the skin. The clinical device includes one or more sensors and electronics for measuring temperature and transmitting the data respectively.

In another embodiment, the clinical device includes a processor located within the body of the clinical device and is programmed to compute fertility information based on the measurements from the sensors.

In another embodiment the clinical device includes a processor located within the body for measuring temperature and resistivity and determining if the measurements fall within an acceptable range, a display or indicator lights to communicate that a valid temperature has been taken.

In another embodiment the clinical device communicates the raw measurements to other computerized devices.

In another embodiment a clinical device comprises a plurality of sensors including a temperature sensor and an electrical resistivity sensor. The clinical device simultaneously collects and processes the data to predict ovulation information.

In another embodiment the clinical device is adapted to relay the measurement or interpretation of bio-medical data to another computerized device such as a mobile phone, tablet, wireless network, computer, watch, or other computerized device. The computerized device being programmed to analyze, record, display, and otherwise manage the data for the user.

In another embodiment, a clinical apparatus includes a skin sensor. The skin temperature sensor measures temperature of the skin. The apparatus supplies the data to a processor for computing fertility information.

In one embodiment, the clinical apparatus allows the user the option of using either a) a combined body temperature and saliva resistivity device data, and/or b) a skin temperature sensor data. The processor is programmed with software adapted to receive and analyze data from any combination of the basal body temperature, skin temperature sensor, and electrical resistivity sensor depending on the user's choice.

In another embodiment, a portable computing device comprises a receiver for wirelessly receiving information; and a processor in communication with the receiver, the processor being programmed with a first software. The processor being operable to receive a first temperature data and an electrical resistivity data of a user and to calculate a level of fertility of the user based on the first temperature data and the resistivity data.

In another embodiment, the processor is further operable to perform the calculation based on temperature data from a second source (such as skin temperature).

In another embodiment, the processor is further operable to perform the calculation based on hormone data from a second source (such as a luteinizing hormone test).

In another embodiment, the processor is further programmed to instruct the computer device to wirelessly transmit the temperature and resistivity data.

In another embodiment, the processor is further programmed to prepare the temperature and resistivity data for third-party fertility software application running on the device to be utilized in the third-party fertility software application.

In another embodiment, the processor is operable to identify changes in the temperature over a time period, and to identify changes in the resistivity over the time period.

In another embodiment, the processor is operable to determine a minimum temperature value and a minimum resistivity value over the time period.

In another embodiment, a processor is operable to determine an ovulation time window based on a range of temperature values and a range of resistivity values.

In another embodiment, software on a storage media includes a set of instructions allowing a clinical device to interact with other or third-party programs, applications, or software. In one embodiment, the software reformats biomedical data arising from the clinical device for syncing or importation into another third-party program on the portable computing device, or cloud-based platform or gateway such as the Qualcomm 2net Hub.

In another embodiment, a programmed processor is operable to share the biomedical data from the clinical devices described herein with other third-party software. An add-on (or plug-in) runs with the third-party software and interacts with the native or host clinical device application to import, sync, or otherwise utilize the biomedical data.

In another embodiment, a programmed processor is operable to detect patterns from multiple indicators including those collected by the clinical device in data sets from a plurality of women for making predictions related to fertility, infertility and the onset of menopause.

In another embodiment, a programmed processor is operable using artificial intelligence techniques to determine predictions out of data sets which include data collected from the clinical device and multiple indicators collected from a plurality of women related to fertility, infertility and the onset of menopause.

In another embodiment, a method of transmitting temperature data comprises the steps of sensing the temperature, processing the temperature, transmitting the temperature.

In another embodiment, a method of tracking temperature, especially for fevers and basal body temperature for fertility monitoring, comprises the steps of relaying the temperature measurement and date/time to a mobile phone, tablet, wireless network, computer, other computerized device, or cloud-based platform or gateway such as the Qualcomm 2net Hub.

In another embodiment, a method for predicting ovulation in a mammalian female comprises the steps of analyzing, preferably, daily measurements of the electrical resistivity of her saliva and/or cervical fluid.

In another embodiment, a method of transmitting temperature and electrical resistivity data comprises the steps of sensing the temperature and detecting the electrical resistivity with a first clinical device, and transmitting the temperature and electrical resistivity data wirelessly from the first clinical device, wherein the first device is a single handheld cable-free device.

In another embodiment, a method for determination of a fertile window comprises the steps of collecting, analyzing, predicting and transmitting combined temperature and electrical resistivity data for determination of a fertile window.

In another embodiment, a method for determination of a fertile window, or fever tracking comprises the steps of collecting, analyzing, predicting and transmitting temperature and/or electrical resistivity data from multiple devices for determination of the fertile window, or fever tracking.

In another embodiment, a method of tracking temperature, especially for fevers and basal body temperature for fertility monitoring, comprises the steps of relaying the temperature measurement and date/time to a mobile phone, tablet, wireless network, computer, or other computerized device.

In another embodiment, a method using software for analyzing measurements for determining fertility, comprises the steps of: analyzing the patterns of the electrical resistivity and the basal body temperature measurements to determine fertile and infertile phases window, and for identifying potential clinical situations based on patterns in cycle-length, temperature and/or the electrical resistivity of saliva or cervical fluid (such as hyperthyroidism, short luteal phase, etc.)

In another embodiment, a method using software for analyzing temperature measurements to determine fever patterns and alerts, comprises the steps of: analyzing data about the age of the subject, the place the temperature is measured from (oral, rectal axillary, etc.), and medicines and doses given to the subject.

In another embodiment, a method comprises storing the body temperature and electrical resistivity measurements with information about the time and date.

In another embodiment, a method comprises graphically displaying biomarker data together with calendar information (chart, visual, or numerical summary).

In another embodiment, a method comprises, using software, electronically transmitting, printing, and sharing biomarker data and calendar information (chart, visual, or numerical summary).

In another embodiment, a method comprises, using software, electronically overlaying and sharing biomarker, and calendar information (chart), and fertility status.

In another embodiment, a method comprises, using software, alerting others according to fertility status.

In another embodiment, a method comprises, using software, alerting others by analysis of fever patterns or thresholds.

In another embodiment, a method comprises receiving other information or data including but not limited to information about bleeding, sexual intercourse, presence and quality of cervical fluid and intake of drugs (such as follicle stimulators). In one embodiment, the method inputs the information in a calendar or chart, and analyzing the information to determine fertility information or ovulation windows.

In another embodiment, a method comprises taking the temperature and relaying the data with a time stamp to a computerized device for record keeping, pattern detection such as a fever spike, and to provide alerts.

In another embodiment, a method comprises taking the data and sending the data wirelessly directly to available devices so that the data can be available for fertility monitoring and fever tracking software, and to detect patterns.

In another embodiment, a method comprises collecting temperature data and data to predict ovulation based on the electrical resistivity of saliva or cervical fluid that transmits the data wirelessly.

In another embodiment, a method comprises computing whether measurements fall into probable ranges; sending the data to a mobile phone, tablet, wireless network, computer, other computerized device, or cloud-based platform or gateway such as the Qualcomm 2net Hub.

In another embodiment, the step of sending the data comprises time/date information.

The description, objects and advantages of the present invention will become apparent from the detailed description to follow, together with the accompanying drawings.

BRIEF DESCRIPTION OF THE DRAWINGS

FIG. 3B is a flow chart of a method to communicate between the clinical device and software when using an add-on.

FIG. 9 is a flow chart of a method to transfer data through a software add-on.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Unless otherwise stated, a trend in the measured data may refer to a trend in the data of an individual user of the device. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Temperature Measurement

Described herein are various clinical devices for measuring or obtaining biomedical data, namely temperature. The clinical devices are also configured to send the data to an external computerized device for processing, display, or communication.

Figure 1:
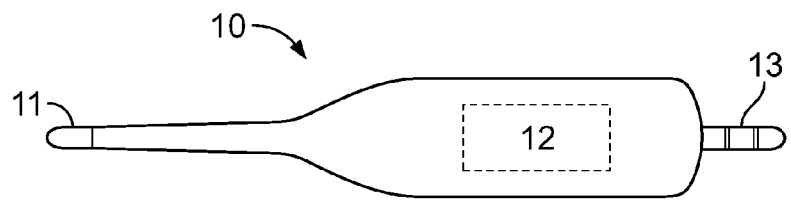
FIG. 1 is a front view of a clinical device.

FIG. 1 is a front view of a first clinical device or thermometer 10. Thermometer 10 is shown including a temperature sensor 11 (e.g., thermistor, thermocouple, or infrared thermometer) and a male connector 13 enabling the thermometer to attach to a female connector or port of, for example, a computerized device or reader. The thermometer, and the/or the computerized device processes the temperature data, as will be discussed in more detail herein.

An example of a connector 13 is an audio jack. The audio jack 13 may be designed to attach directly to the computerized device, or via a flexible cable linked to the computerized device. A non-limiting exemplary technology for communicating data with an audio jack is the Hijack Project (created by the CSE Division/EECS Department at the University of Michigan, Ann Arbor), a hardware/software platform for creating sensor peripherals for mobile phones. In an alternative embodiment, the thermometer includes a USB cable extending from its body, and which can connect to the USB port, a mini USB connector, or other data transfer or docking port of a computing device.

The clinical device or thermometer 10 may include a number of additional components including, e.g., a processor 12, memory, battery, display, buttons or inputs, and other electronics typical of a digital thermometer. Additional internal electronics may include, e.g., a clock, an LCD or LED display or lights in the more proximal end, or the body, of the thermometer 10. Additional electronics such as a processor and amplifier or USB interface may be included to support the communication with another computerized device via the audio jack or USB port as is known to those of skill in the art.

The probe tip may be constructed of flexible material for comfortable insertion into the mouth and vagina, and in the case of an infrared sensor, it may include a spacer to create a distance between the sensor and the inside of the mouth. An example of a probe is described in US Patent Publication No. 2005/0226307. Preferably, the distance-to-spot ratio ranges about 1:0.18 to 1:0.25.

Figure 2A:
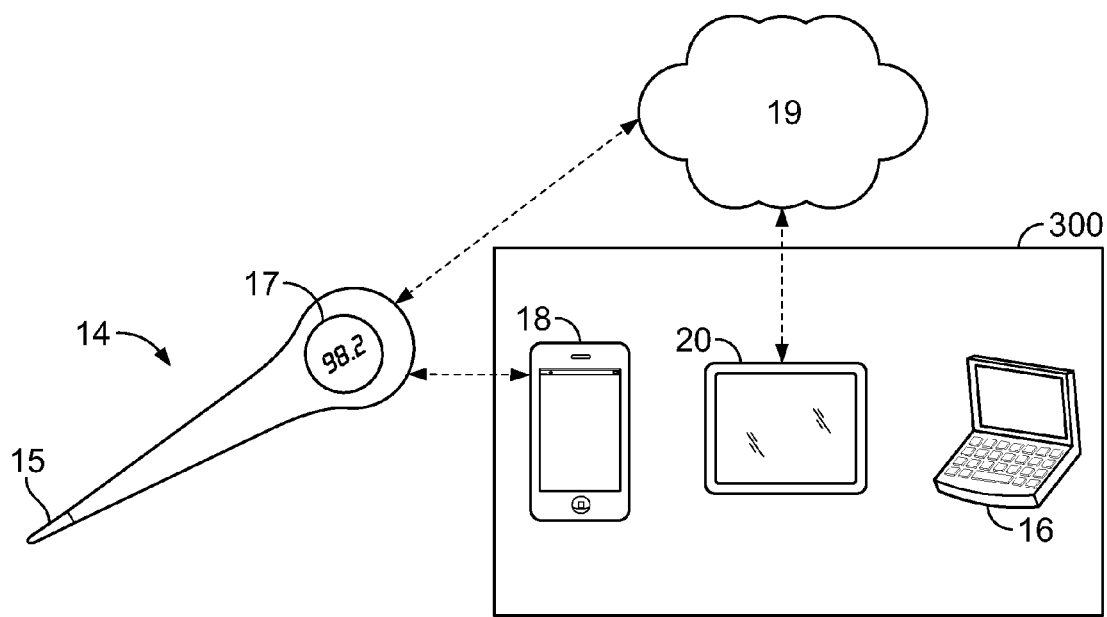
FIG. 2A is an illustration of a system including a clinical device, communicating with various computerized devices.

FIG. 2A is an illustration of another clinical device for measuring temperature. The clinical device 14 shown in FIG. 2C, however, is wireless. It is adapted to wirelessly communicate with various computing devices 300 including but not limited to a laptop computer 16, smart phone 18, or tablet 20.

The clinical device 14 may also communicate data to other types of devices such as watches, bracelets, or other computerized devices and receivers that may be worn (e.g., necklace or armband carrying a small portable receiver). Additional examples of types of receivers include those described in Patent Publication Nos. 20050245839 and 20020019586. Indeed, a wide range of computing devices or readers may be configured and/or programmed to receive data from the clinical device 14 and to compute a fertility grade, alert, feedback, or monitoring result, as will be described in more detail herein. Exemplary types of feedback include ovulation prediction, diagnoses related to fertility, recommendations of treatments or interventions, recommendation for treatment of infertility, management of subfertility and other gynecological disorders such as luteal phase deficiency or short luteal phase, management of premenstrual mood disorders, and treatment or identification of premenopausal or menopausal systems.

With reference to FIG. 2A, data is collected by clinical device 14 and the raw or processed data (e.g. temperature) is transmitted to one or more of the various receiving devices 300. Data may sent to the computerized devices 300 in various manners including without limitation: a) through the cloud 19 to the receiving devices (e.g., over wireless local area networks which might include cellular and/or IEEE 802.11x (including all generations, amendments, or variations also known as WiFi) to a server or another computerized device through protocols such as Internet); or b) directly to the computerized devices using wireless communication technologies (particularly those that utilizes radio frequencies and protocols such as Bluetooth, Zigbee, NFC (near field communication), or other short-range wireless technologies), infrared, or ultrasonic. Examples of wireless techniques to transmit data from biosensors are described in U.S. Pat. No. 6,336,900 to Alleckson, and U.S. Publication No. 2005/0101841 to Kaylor.

Computerized devices lacking internal hardware to wirelessly receive data may be equipped with accessories to make them capable of wirelessly receiving data. For example, certain dongles may be connected to the USB port of a computer, making the computer capable of WiFi or other RF communication. An exemplary dongle is the ASUS USB-BT211 Mini Bluetooth Dongle USB 2.0 dongle (Manufactured by ASUS, Taiwan, R.O.C).

The clinical device 14 may be provided with a wide area wireless chip or equivalent for direct telecommunication with other devices or through a network. The clinical device 14 may transmit its data to such a chip in a cell phone or other device that includes wide area wireless functionality, which may then forward the information anywhere in the world via the Internet. Additional electronics may be included within the clinical device 14 to support the communication with other computerized devices to the cloud or directly to a computerized device, such as a transmitter and/or a transceiver as will be discussed in more detail herein.

Clinical device 14 is shown having a display 17 indicating temperature measurement. The display 17 is shown being located in the body of the thermometer, towards the proximal end.

Display 17 may also be operable to include other functions such as but not limited to a back-light, alarm set function, user's degree of fertility, battery charge indicator, status of measurements, rate of completion of measurements to give positive feedback to the user for using the device, and/or to give the user feedback about the accuracy of previous predictions related to her fertile window. These functions may alternatively be available from the computerized device.

Clinical device 14 may also include an accelerometer or jiggle switch. Such a switch may detect when the user picks up the device. In one embodiment the alarm is turned off when the device is picked up. In another embodiment, the user is rewarded for her picking up the device (for example with lights, sounds or vibration).

Figure 2C:
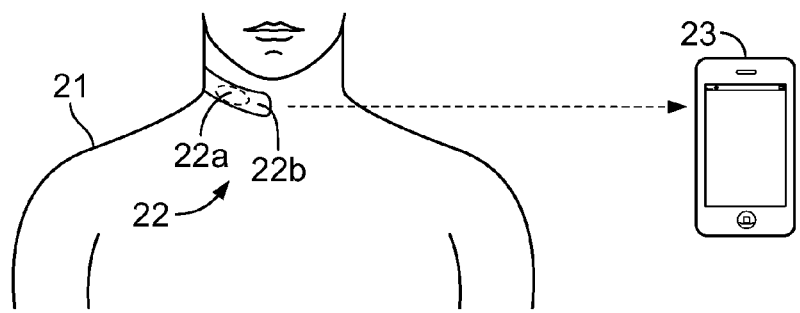
FIG. 2C is an illustration of a skin sensor thermometer in an application and communicating with a computerized device.
Figure 2B:
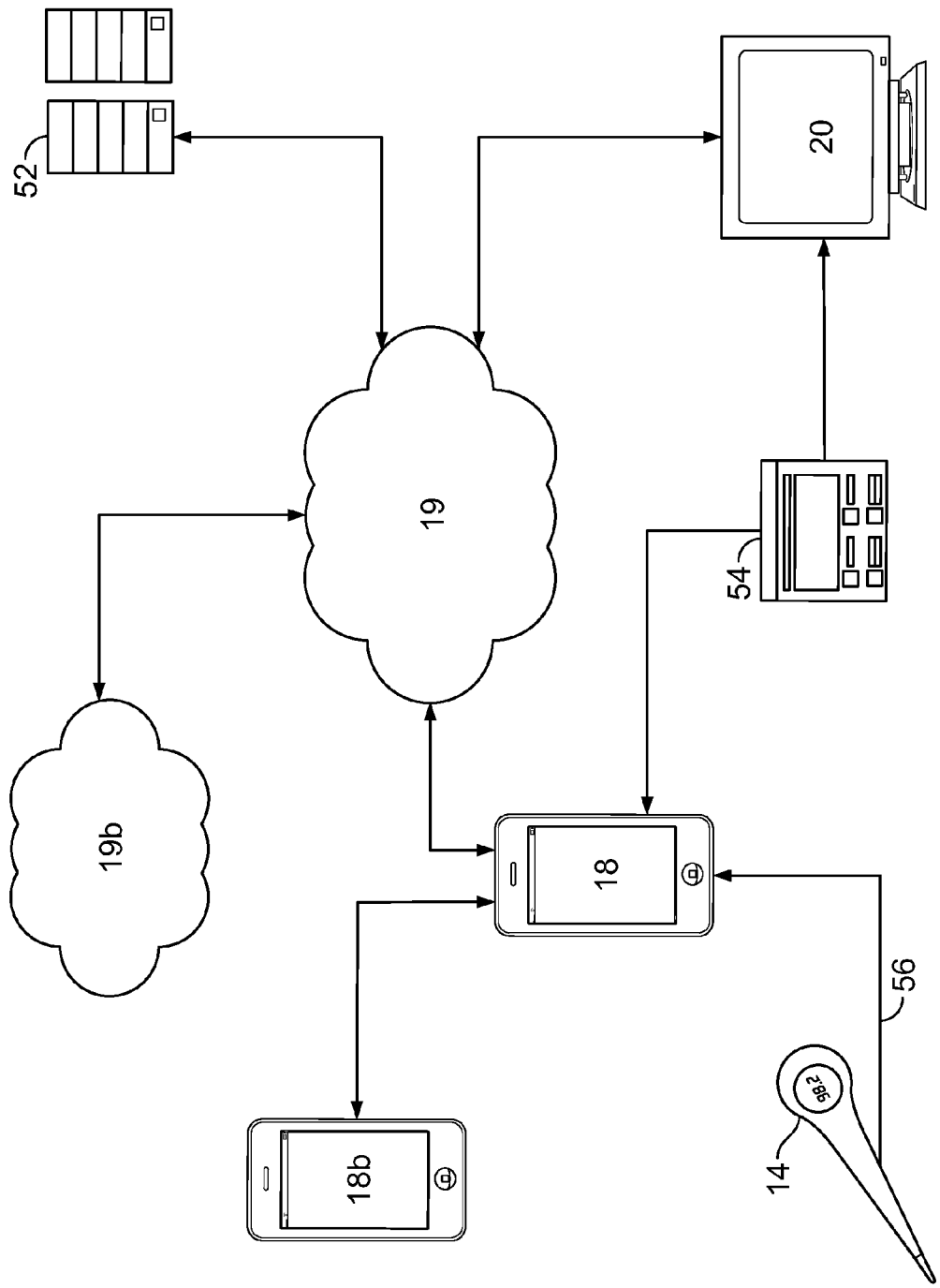
FIG. 2B is an illustration of a fertility monitoring system including a clinical device, computerized devices, and servers.

FIG. 2B shows a system comprising a clinical device 14 adapted to measure various physiological data of an individual (e.g., temperature), a computerized device 18 (e.g., a PDA, tablet, or smart phone), a platform server 52 (e.g., a server programmed to register the user and to accept multiple inputs through a secure web site/web portal), and another computerized device 20 adapted to connect to the server (e.g., a laptop or desktop or tablet).

Preferably the server stores the data from a plurality of users in data sets for the discovery of patterns using methods known to those skilled in the art of machine learning, artificial intelligence, predictive analytics, statistical modeling, and database systems.

The smart phone 18 is preferably programmed with a first software (e.g., a first app) which includes methodology and steps to predict and determine the user's fertile window as will be described in more detail below.

A secondary optional smart phone 18b may be programmed with another version of the first software (or a second software or second app) designed for a woman's partner and includes updates, alerts, and health tips for supporting male fertility, and calendar synchronization for example, Apple iCAL®, Microsoft Outlook®, etc. This step could be automatic, and enable synchronization of various data as described herein including but not limited to the user's period, and fertile window.

FIG. 2B shows communication directly between computerized devices (illustrated here with smart phones) or via the cloud. However, in addition to receiving signals directly, the cloud 19 may also receive medical data via an electronic or personal medical record 19b for incorporation into the user's data set.

The server 52 is preferably programmed with a server or third software, namely, a web platform including a database for inputting the user's information and history and for comparing the data from a plurality of users in data sets for the discovery of patterns using methods known to those skilled in the art of machine learning, artificial intelligence, predictive analytics, statistical modeling, and database systems. For example, the platform may make use of recursive partitioning algorithms for making dynamic assessments of pattern matching of the aggregated data with an individual user's data to apply predictions or recommendation related to fertility.

The server 52 may also be programmed to discover and provide information and recommendations to individual users about how to manage gynecological disorders, monitor her fertility, improve chances of conception, and/or avoiding pregnancy.

In embodiments, the server is programmed to receive one or more inputs. Example inputs to the server include static inputs (e.g., birth date, height, medical history) from the user's profile. Such inputs may be communicated to the server through a website using a computerized device to connected to the internet.

In embodiments, the smart phone's software, such as an app is programmed to receive one or more inputs. Example inputs directly to the smart phone 18 include additional static inputs (e.g., date of last period, cervical fluid observations, notation of coitus). Additionally, participatory health research inputs 54, such as electronic surveys regarding fertility (e.g. family fertility history, the use of fertility interventions) may be communicated to the server through a website using a computer device 300. Additionally, in embodiments, the smart phone or portable computerized device is programmed to receive one or more dynamic inputs. Examples of dynamic inputs include but are not limited to date and time reference points.

Additionally, raw or processed data 56 (such as but not limited to pre-screened temperatures to fall in certain parameters) is received by the smart phone from the clinical device, and stored.

The smart phone additionally obtains system inputs such as time zone and time information.

As will be discussed in more detail herein, the portable computing device is programmed to carry out a number of steps including but not limited to calculating a fertility window based on the dynamic, static, system, and data inputs mentioned above.

Further, the system learns from the data collected from the individual user and from the aggregated data to improve upon, or self-modify calculations using machine learning or artificial intelligence approaches.

In embodiments, a central fertility platform includes wirelessly connected clinical devices, and a database of aggregated information related to fertility for multiple users. Fertility encompasses menopause and includes statistical analysis related to menopause predictions. Information input from the user's account via web and cloud is fed into an algorithms run on the portable computerized device. Information includes but is not limited to the user's cycle length, diagnosis of fertility, reproductive health information. Feedback encompasses diagnosis related to fertility, recommendations of treatments or interventions, treatment of infertility as far as timing of treatment procedures, management of sub fertility and other gynecological disorders such as luteal phase deficiency or short luteal phase, management of premenstrual mood disorders, and treatment or identification of premenopausal or menopausal systems.

Skin Sensor Temperature Measurement

FIG. 2C shows another clinical device 22 for sensing data and in particular, for measuring skin temperature. The skin sensor thermometer 22 shown in FIG. 2C is positioned on the base of the neck of a user 21. In this embodiment, similar to that described above, electronics within the patch or pad-like thermometer 22 communicate directly to a computerized device such as the mobile phone 23 illustrated in FIG. 2C (but also includes the possibility of communicating wirelessly over the internet to a server or directly to another computerized device as described above). Preferably, as described above, the skin sensor thermometer 22 includes a temperature sensor 22a, and a base or body member 22b which supports the sensor. The base also holds or supports other components such as a transmitter, memory, ID, and an energy/battery source. In an alternative embodiment, energy is transferred from another external source, such as a stand, to the device by a capacitor or rechargeable battery (or hybrid battery) as it is known to those of skill in the art.

In yet another embodiment, energy is harvested or scavenged while the user wears the skin sensor from thermal or kinetic energies (including blood flow) produced by the human body by methods known to those having skill in the art. For example, the Nike Lunar TR1+ shoe line that harvests energy from the pressure of the shoes to power embedded sensors, or solutions being explored by Ambient Micro (of Half Moon Bay, Calif.) and the Body Sensor Networks with the Royal College of London (London, UK) that provide energy for biomedical applications. Alternatively, energy is harvested from radio waves as being developed by the School of Electrical Engineering and Computer Science at Oregon State University.

The location of the skin sensor thermometer 22 may vary. Although it is shown located at the base of the neck, the skin sensor thermometer 22 may be placed or worn at other locations that are determined to give a good representation of basal body temperature.

The base 22b shown in FIG. 2C is substantially planar, and preferably conforming. However, the device 22 may have other shapes. The base 22b may also include an adhesive or strap to facilitate attachment to a proper anatomical location.

The skin temperature sensor 22a may be disposed outside the housing 22b, and/or the ambient temperature sensor may be affixed or reside on the surface of the housing, and it may be included in some other form such as a bracelet. The data from the skin sensor is transmitted, and processed as described herein.

Figure 3A:
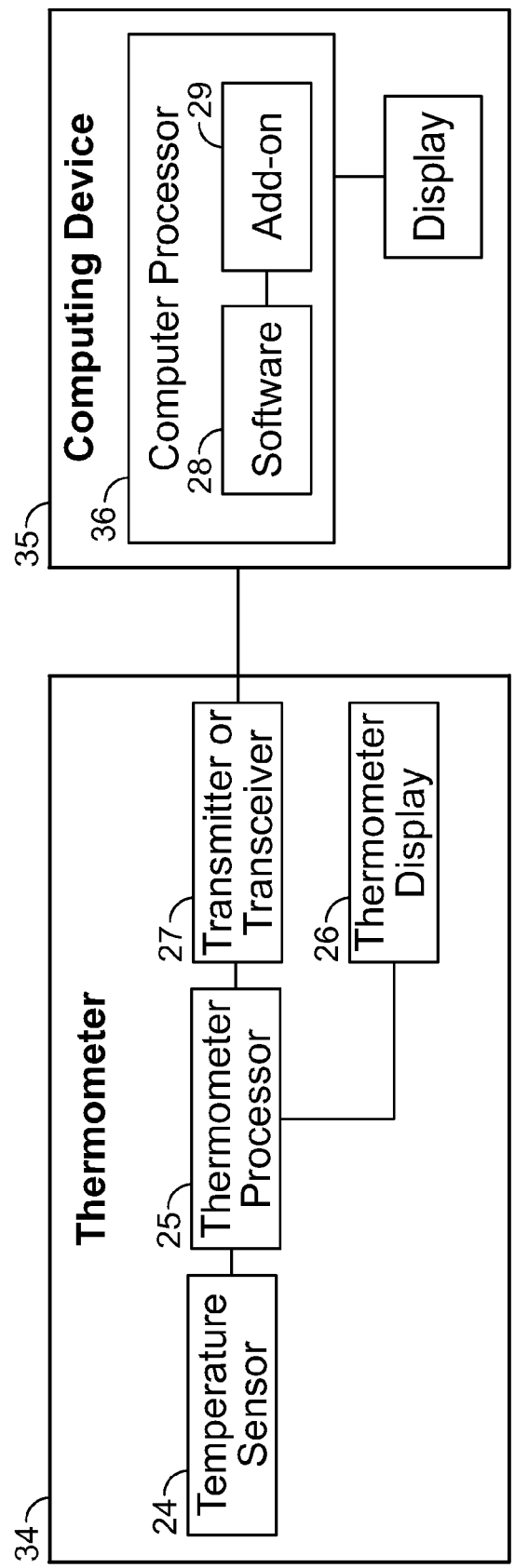
FIG. 3A is a block chart showing components of the clinical device's thermometer and a computing device.

FIG. 3A is a block diagram or chart showing communication between a thermometer 34 and a computerized device 35. Although communication is shown being carried out directly from the thermometer to the computerized device 35, in an alternative, the data is transmitted remotely over the Internet to a server or another computerized device.

With reference to FIG. 3A, the clinical device 34 is shown having various electronics including a temperature sensor 24, a temperature processor 25, a display 26, and a transmitter 27. The processor 25 calculates a measurement from the temperature sensor 24 and communicates the measurement to the thermometer display 26 (if included), and the transmitter or transceiver 27 (or in the case of FIG. 1, additional electronics to convert the audio port signal to the computerized device it is connected to).

The transmitter or transceiver 27 is configured to wirelessly communicate with the computerized device 35 such as a laptop computer, smart phone, or tablet. The computerized device is shown having a processor 36 programmed with software 28 and perhaps various add-ons or plug-ins 29 (if included). The software includes various steps, as will be described in more detail herein, to prepare, determine or calculate various fertility-related outputs based on data received from the thermometer 34.

Figure 3B:
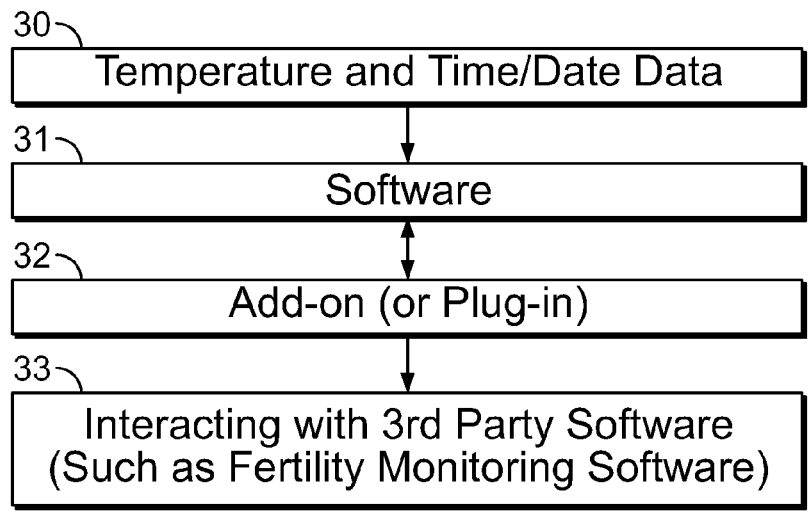

FIG. 3B is a flow chart of a method for using a thermometer with software running on computing device 35. The method illustrated in FIG. 3B comprises obtaining temperature and time/date data and sending it to a computerized device (step 30). This may be carried out using a clinical device described above.

The next step shown in FIG. 3B states software. This step involves use of software running on a computerized device programmed with a first software to retrieve and process the data (step 31). Optionally, the first software has a means or steps to compute fertility information based on the data.

The next step shown in FIG. 3B states add-on or plug-in. This step comprises preparing or setting-up the data to facilitate transferring the data to appropriate fields of a third-party software such as a third-party fertility software (Step 32). Examples of third-party fertility include the iPhone app from FertilityFriend of the Province of Ontario, Canada. This step may be carried out with a second software portion or module loaded and run on the processor such as a plug-in. The plug-in may operate with, and can be integrated with the third-party software. The microprocessor on the clinical probe may encrypt or encode the data and the plug-in might decode the data as part of the preparation to transfer data to the third-party software.

The last step shown in FIG. 3B comprises interacting with the third-party software, namely, sending, syncing, importing, or otherwise transferring the data in the proper format to the third-party software so that the user may utilize the third-party fertility software with the temperature time/date data from the thermometer described above (step 33).

A wide variety of third-party software and applications may conveniently accept and process the temperature and other data from the clinical devices described herein. The users shall not be required to manually input data supplied by the clinical devices herein. The data shall be syncable or importable in the convenient automatic manner described herein. Alternatively, a standalone software may be provided with the computing device to predict ovulation and alerts based on the temperature data.

Electrical Resistivity

The clinical device described herein may include a wide variety of sensor technologies. In addition or in the alternative to the temperature measurement probes described above, the clinical device may be configured to measure electrical resistivity (or impedance if the resistance is measured with an AC current) of saliva or cervical fluid. Indeed, in one embodiment the clinical device or probe includes a plurality of sensing modalities.

The variation or resistivity observed in saliva and cervical fluid is reflective of the their ionic fluid which is influenced by the interaction of estrogen and progesterone in a woman's body. While electrical resistivity is discussed herein, the same effect of measuring the total electrolyte concentration of the saliva and cervical fluid can be achieved by measuring electrical impedance or conduction.

Creating a fertility monitoring device which captures temperature data and electrical resistivity data greatly improves the accuracy and convenience over single modality devices. By combining the measurements of these two data types in one easy to use device, women can have an improved method of monitoring their fertility.

Figure 4A:
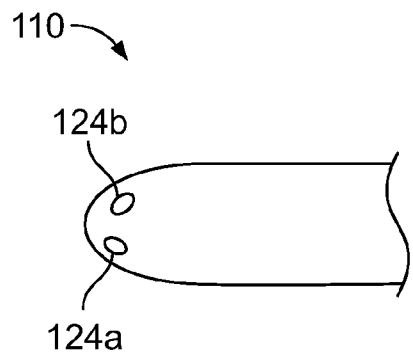
FIGS. 4A-4B are partial side views of various probes to measure saliva resistivity.
Figure 4B:
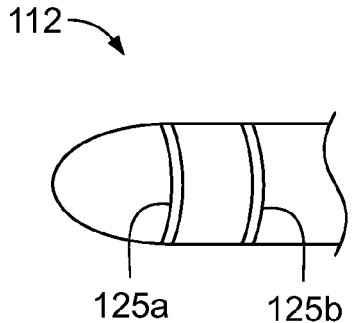

FIGS. 4A-4B show partial side views of tip of the probe on the distal section of the clinical device comprising sensors for measuring electrical resistivity or impedance.

FIG. 4A shows a probe tip on the distal section 110 comprising two sensors or electrodes 124a, 124b having an oval or cap-like shape. FIG. 4B shows a probe tip on the distal section 112 comprising two sensors or electrodes 125a, 125b having a cylindrical or ring-like shape. Each ring and cap is connected internally to a wire. The wires run from the distal section, or sensing end, to the proximal section, or body, of the device. In one embodiment, the wires extend through a probe handle for connection to the electronics, described herein. Although not required, the electrodes preferably are embedded so as to provide a smooth exterior surface. The electrodes are separated by a distance. An exemplary range for this distance is between 0.1 and 2 cm.

Two configurations of the sensor electrodes 124 and 125 are shown here. The sensor electrodes may be formed of a wide variety of materials. The sensor electrodes are electrically conducting. Exemplary materials for the electrodes include but are not limited to stainless steel, Gold, Platinum, Rhodium, or a like material that is resistant to corrosion.

An embodiment comprises at least two sensor electrodes. In this embodiment, the electrodes are embedded in non-conducting material, such as plastic or silicone. Where more than two sensor electrodes are included the electrodes could be wired in a configuration with alternating electrodes electrically connected together. The same electrical effect may be achieved using alternative methods, such as with printed circuit board technology. Additional non-conducting materials may be applied to achieve the desired effect for measuring electrical resistivity.

Figure 4C:
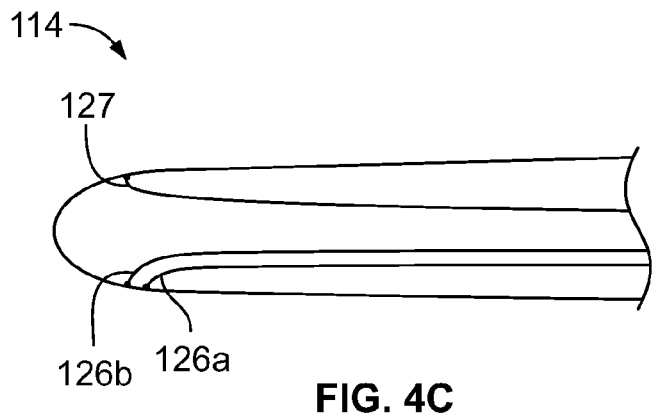
FIG. 4C is an interior side view of another probe to measure saliva/cervical fluid resistivity and temperature.

FIG. 4C is a partial cut-away view showing the interior body of a clinical device 114 which may be used to predict ovulation. Ovulation is predicted by monitoring changes in saliva and cervical fluid. When the clinical device is inserted into the body (mouth or vagina), the saliva or cervical fluid (respectively) covers the tip of the probes. A current is sent through the electrodes 126a, 126b via the metal electrodes and ions in the saliva or fluid. The electrodes are connected to the clinical device's electronics most likely by at least one shielded conductor. Resistance or impedance is measured with an electronic circuit described in more detail below. In saliva, a rise followed by a drop in the impedance determines the approach of ovulation explained in more detail in the description of FIG. 6. Also visible in FIG. 4C is a temperature sensor 127, which is similarly placed on the distal tip and is connected by wires to the clinical device's electronics.

Figure 5:
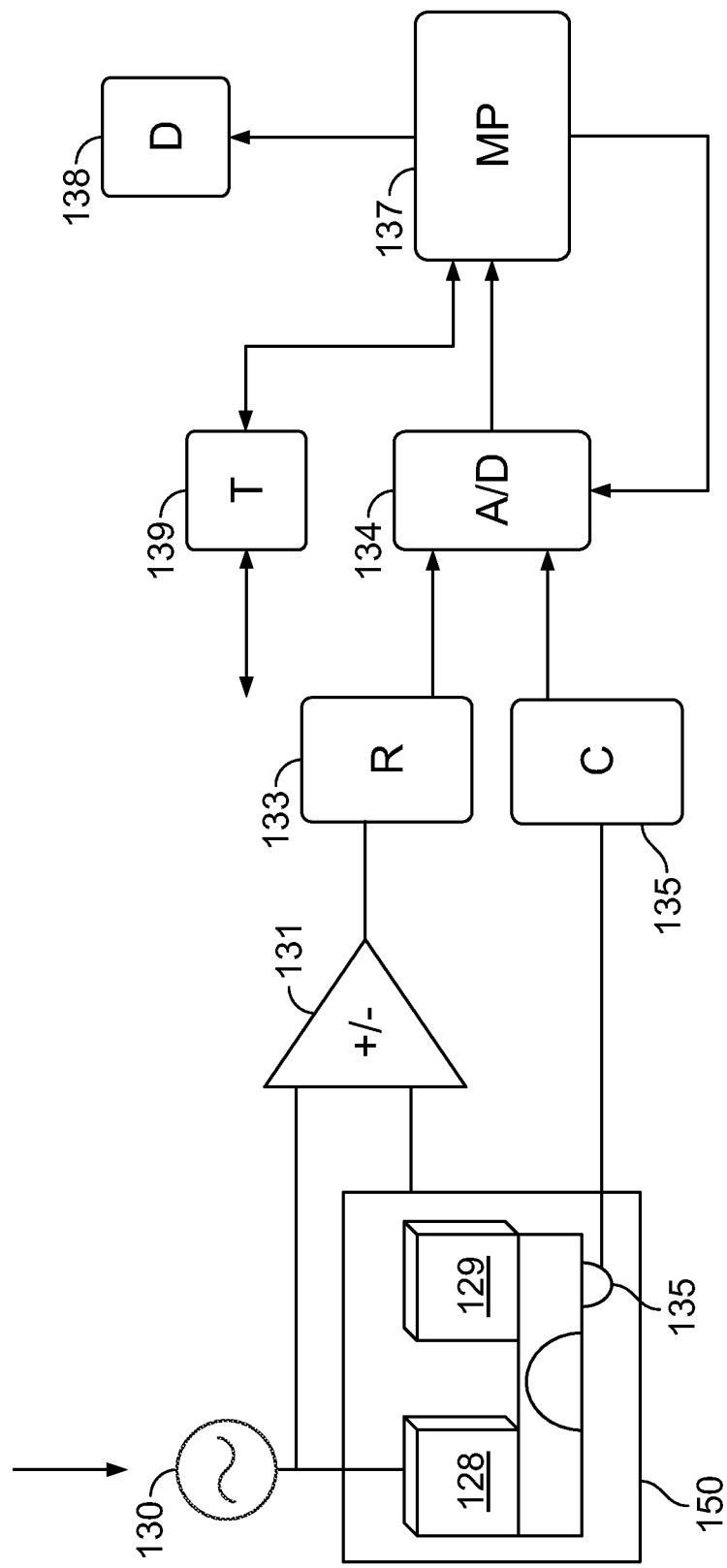
FIG. 5 is a block diagram of components of a clinical device for measuring electrical resistivity (or impedance) of saliva or cervical fluid.

FIG. 5 illustrates a diagram of a clinical device containing circuitry to measure the electrical resistivity of the saliva or cervical fluid and to measure temperature (in this case a thermistor). Clinical device includes a distal probe portion 150 that is designed and constructed to be inserted into the body (preferably the mouth or vagina), which includes electrodes 128, 129 at a certain distance from each other. A non-limiting shape for clinical device is that set forth above in connection with the thermometer device, and the probe distal section shown in FIGS. 4A-4C.

With reference to FIG. 5, electrodes 128, 129 are shown connecting to an alternating current source 130, and to an amplifier 131, the output of which connects to a rectifier 133 which is connected to a dual-input A/D converter or V/F converter 134.

Temperature sensor (thermistor or infrared) 135 is shown in distal probe sensing section 150 and also connects to an amplifier and A/D converter or V/F converter in the probe via a signal conditioner 136. The signal conditioner converts resistance (for a thermistor) or voltage (for a thermocouple) into a voltage at the A/D or V/F converter using techniques known to those skilled in the art. In IR thermometer uses a thermopile or thermocouple, which may have a similar signal conditioner.

The A/D or V/F converter is connected to a microprocessor 137. In one embodiment the microprocessor is operable to compute (e.g., to predict and confirm) whether there is ovulation based on an algorithm relating to the resistivity or impedance measurements during ovulation and the temperature measurements. Processor 137 sends this information to the display 138 (if included). Processor may send information to a transmitter or transceiver 139 for transmitting information wirelessly to a mobile computerized device, such as a smart phone, or to the internet and cloud.

In another embodiment, the clinical device transmits the resistivity or impedance and temperature measurements to an external computerized device, such as a smart phone, where fertility and ovulation is predicted or confirmed by the external computerized device. The data or input can thus be sent via distinct channels and computed separately, the results which can be displayed on the clinical device itself and/or on another portable computerized device having been transmitted wirelessly. Information regarding fertility phase may be presented in detail with measurements or summarized with graphics, signs, lights or words on the computing device that it communicates with, or the clinical device itself.

Figure 6:
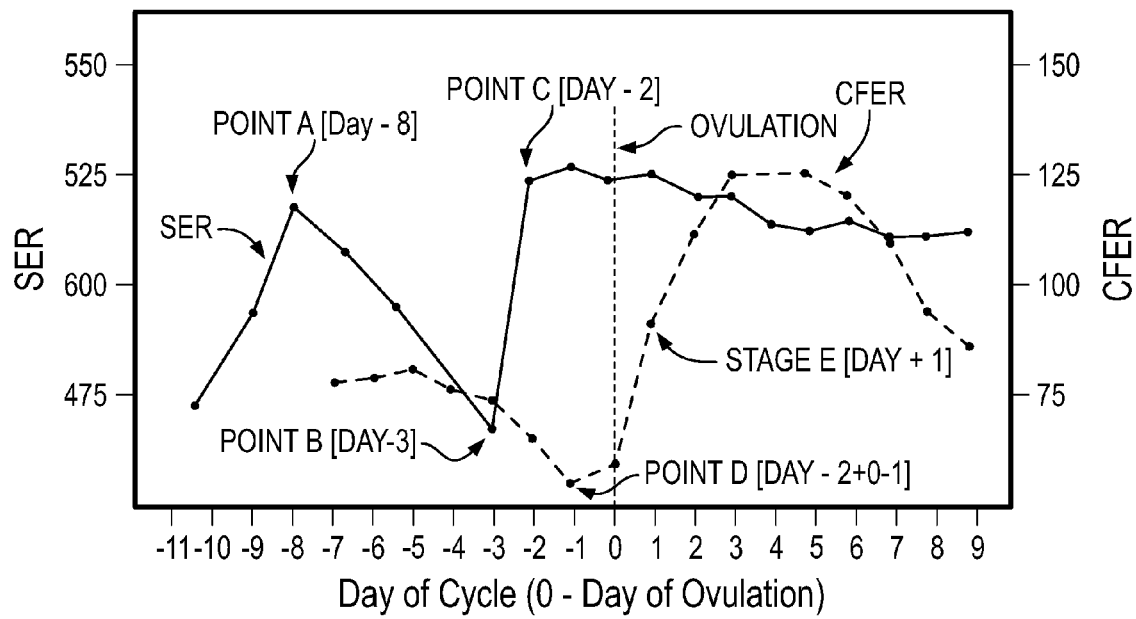
FIG. 6 is a graph of saliva electrical resistivity (SER) and cervical fluid electrical resistivity (CFER) over a menstrual cycle.

FIG. 6 is an example of a diagram showing a sample menstrual cycle with saliva electrical resistivity (SER) and cervical fluid electrical resistivity (CFER) measurements from which ovulation can be predicted. The onset of ovulation could be determined by identification of a peak (Point A on FIG. 6) in electrical resistivity measurement at the beginning of a menstrual cycle followed by a nadir (Point B on FIG. 6) and subsequent sharp increase in the electrical resistivity or impedance measurement (Point C on FIG. 6). Ovulation is predicted approximately 8 days from Point A, three days from Point B, and 2-3 days from Point C. For cervical fluid, the onset of ovulation shows a nadir in electrical resistivity measurement (Point D on FIG. 6) on the day before ovulation, followed immediately by a rise in resistivity after ovulation. The algorithms used to determine these various points may combine resistivity, temperature measurements along with cycle day, cycle length, and user history. The algorithms eliminate noise or aberrations so as to identify significant variation in resistivity and BBT measurements.

In an embodiment of the invention disclosed herein, the resistivity and BBT measurements are used by algorithms to determine the fertile window (including, e.g., prediction and confirmation). Further, as the system collects data and history patterns, and cycle day information, the algorithms use this data in combination with the resistivity and BBT measurements in determining when the user is fertile.

At the beginning of a menstrual cycle, a first step could compare the SER from the previous day looking for a rise in value. When the slope value changes from a positive to negative, it signals that Point A was reached in the previous 24-48 hours and conception is possible through the day after ovulation.

A second step detects Point B by the reversal of a negative slope of the SER measurements to a positive slope signaling that ovulation likely within 3 days.

A third step identifies a subsequent sharp rise SER, confirms imminent ovulation, and identifies Point C which corresponds to the time when the user is notified that she is most fertile. Alternatively, a user may verify ovulation by using the device vaginally measuring the electrical resistivity of her cervical fluid along with temperature, or the system may recommend to the user to take CFER measurements if the SER does not follow an interpretable pattern. CFER measurements are detected along a negative slope until Point D is reached, indicating the nadir described above.

An additional step overrides SER data if it does not follow a predicted pattern and is replaced by other inputs, such as the user reporting that she has "fertile quality" of cervical fluid (defined as clear stretchy and slippery), before a thermal shift.

Finally, Stage E is identified with the dual marker of a thermal shift in BBT and with the continued rise in CFER or gradual decline of the SER. At this point the user is notified that conception is unlikely as Point E and the BBT thermal shift occur through the day of ovulation and the identifying patterns from BBT and resistivity require two days of data input.

Figure 7:
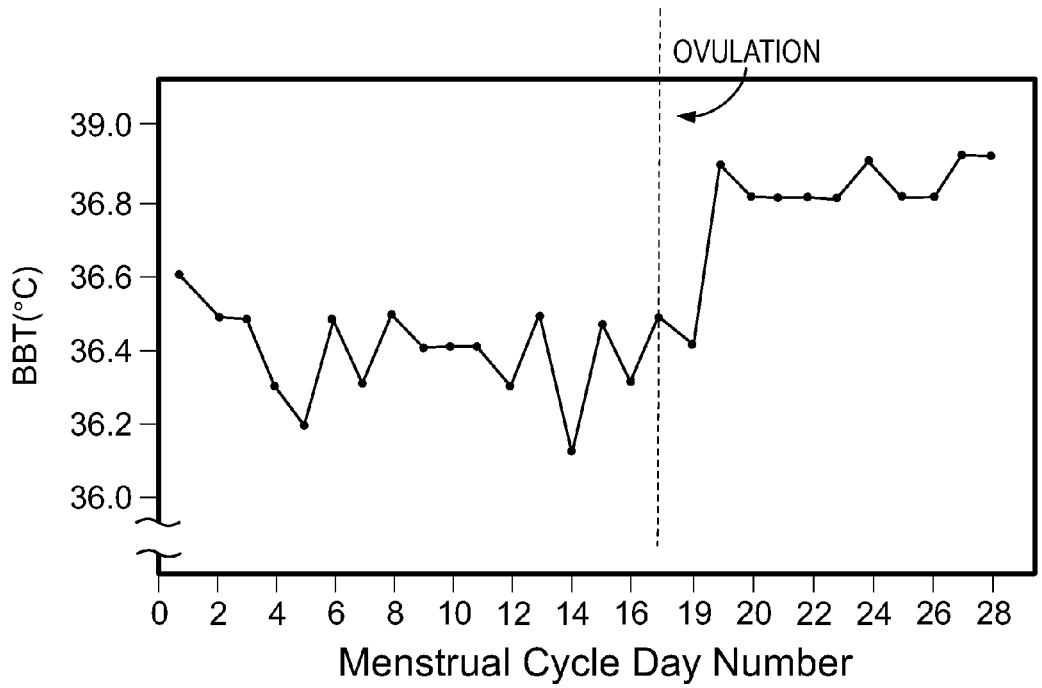
FIG. 7 is a graph showing a sample menstrual cycle with basal body temperature measurements over a menstrual cycle.

FIG. 7 is a diagram showing a sample menstrual cycle with basal body temperature measurements with a thermal shift (a rise between 0.2 and 0.6 degrees Fahrenheit at the time of ovulation). Temperatures typically rise after ovulation (within 24 hours) due to increased levels of progesterone released by the corpus luteum during ovulation. In some cycles and for some women the pattern is less distinct, or bi-phasic, but may still exhibit a more gradual rise near ovulation.

Examples of detecting the thermal shift in BBT are described by Toni Weschler in Taking Charge of Your Fertility, 10th Anniversary Edition: The Definitive Guide to Natural Birth Control, Pregnancy Achievement, and Reproductive Health, Collins; 10th anniversary edition (Oct. 31, 2006), and in J. P Royston and R. M. Abrams in "An Objective Method in Detecting the shift in Basal Body Temperature in Women, *Biometrics*, Vol. 36, No. 2, pp. 217-224 (June 1980) and U.S. Pat. No. 4,475,158 to Elias.

In one embodiment of the present invention, the computerized device is programmed to track time dynamically and take into account travel across time-zones, and day-light savings. A women's basal body temperature rises slowly the longer she sleeps and that in order to detect the thermal shift in BBT, measurements are preferably taken daily at the same time.

Furthermore, distortion to the body's circadian rhythms including basal body temperature patterns and other chronobiological-related problems are brought on by crossing time-zones. When a woman travels across a time-zone or wakes and takes her temperature at a different time, the typical solution is to add or subtract to her measurement accordingly based on a regular wake up time and a regular time-zone.

In an embodiment of the present invention, algorithms compare the time from the recorded time stamp on the clinical device to the time of receipt of the data to the phone and adjusts the temperature measurements without needing to establish a regular wake up/measurement time or regular time-zone by querying the phone's time zone settings, detecting travel outside of a time-zone, and calculating a dynamic reference time wherein the BBT measurements are adjusted accordingly.

In addition to relieving the user the need to adjust her temperature measurements, the method of invention relieves the user from being beholden to a regular wake up time. It also results in more accurate BBT tracking as it is based on real time temperature measurements and not an intended usual wake up time.

Additionally the system may help with day-light savings or jet-lag travel time adjustment when the user is scheduled to travel multiple time zones thereby minimizing disturbance to BBT patterns by proposing a more gradually shifting sleep schedule. This may include querying the phone's calendar for upcoming flight information based on detecting airport codes, flight information or other methods; or querying date, GPS, time, and calendar setting within phone to detected day-light savings events.

A method for calculating BBT measurements (from the clinical device) and associated time stamp includes the following steps:

Step (a) Record first time-stamp generated by the clinical device with the first BBT measurement;

Step (b) Upon receiving of a temperature measurement query the phone's time zone setting, or GPS, to record the associated time-zone.

Step (c) Record second time-stamp generated by the clinical device with the second BBT measurement. If the time difference recorded by the clock on the clinical device is less than a threshold amount (e.g., within 35-50 minutes or about 45 minutes of the first time-stamp), then no time-zone querying is needed and can proceed to dynamic reference time steps.

Step (d). If time difference in time recorded by the clock on the clinical device is greater than the threshold amount then the app queries the phone's time zone setting to determine if the user has traveled outside of her last recorded time zone. For each time zone traveled east, adjust by adding 0.1° C. per time zone (or fraction of) for one day for every time zone crossed. For each time zone traveled west, adjust by subtracting 0.1° C. per time zone (or fraction of) for one day for every time zone crossed. Similarly, as described herein add or subtract to each temperature measurements in relation to increases or decreases in the dynamic reference time.

Step (e) Continue calculating the dynamic reference time. Create a running average time of (adjusted) wake up times. Record the time-stamp of the subsequent measurement. Compare to the time-stamp to the dynamic reference time. For every hour after, subtract 0.1° C. (or fraction of). For every hour before, add 0.1° C. (or fraction of).

Step (f) When a predetermined rise, say 0.25° C. or more for three consecutive days, the thermal shift has been detected.

For new users who have a less distinct bi-phasic pattern, the system may chose to detect the thermal shift by performing cumulative sum statistical test. A method comprises the following steps:

1) Acquiring daily temperature measurements from the device and calculating an average from Cycle Day 4 through Cycle Day 12 to determine a baseline in relation to said dynamic reference time.

2) Once the baseline temperature has been determined in relation to said dynamic reference time, comparing each temperature to the baseline to derive a reference temperature (R). For example a measurement higher than the baseline would be $(x_r-R)$ in which $x_r$ is the daily temperature measurement.

3) Detecting when the cumulative sum of positive deviations exceeds a predetermined threshold, such as, for example, 0.25° C.

4) For every daily measurement acquired, the system could also validate that a temperature has been detected based on a predetermined range calculated by inputs from the user's history, the time taken, and a typical range expected given the SER measurement analysis and cycle date (Pre-ovulatory temperatures typically measuring 97.0 to 97.7° F., and post-ovulatory typically exceeding 97.8° F.). And, when a BBT measurement is invalid, alerting the user to retake the measurements with the clinical device.

In another embodiment the present invention is designed with features to aid in the compliance of regular use of the fertility monitor. Existing tools make fertility monitoring tedious and require the tracker to remember to check or measure various fertile symptoms regularly, and often first-thing in the morning. The high failure rate of tracking various fertility symptoms regularly is a major reason women and doctors don't use them despite their clinical effectiveness.

One embodiment of the present invention minimizes the hassle of fertility monitoring. In addition to the alarm function and the automation of sending data to the software for analysis, the system is designed to increase the users compliance through reward lights, sounds, vibrations, or messages and by creating a dopamine induced loop offering a reward for what would otherwise be a tedious task. In embodiments, the system is programmed to create a game or competition with others tracking their fertility.

Further, in embodiments, the system increases compliance by displaying graphically or mathematically the rate of her use to the user. In embodiments, the system is programmed to send the user a reminder when her use falls below a certain threshold of, say 85%, or a message of encouragement at seemingly random times. In embodiments, the system coaches the user in the monitoring or management of her fertility.

The user's confidence in the system are also supported by calculating and reporting or displaying graphically how accurate the predictions have been in past cycles.

One embodiment of the present invention includes combining measurements of saliva electrical resistivity and/or cervical fluid electrical resistivity with basal body temperature measurements to predict or compute an ovulation window, namely, a fertile phase. Another method includes using the above described information to compute an infertile phase of the cycle. A wide range of alerts, as will be described in more detail below may be provided or indicated to the user based on the computation and measurements.

Figure 8:
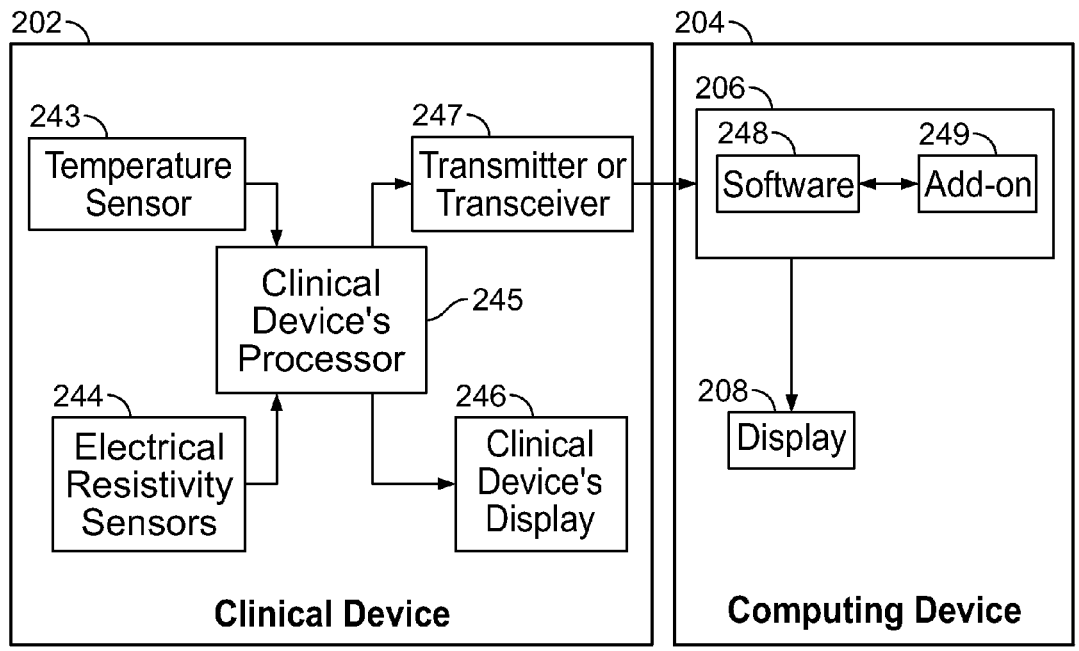
FIG. 8 is a block chart showing components of a clinical probe and a computing device.

FIG. 8 is a block diagram or chart showing the communication links from a clinical device 202 to a computerized device 204. Alternatively, or in addition to, the clinical device may communicate remotely over the Internet to a server or another computerized device as described above.

Clinical device 202 is shown having a number of components including a temperature sensor 243, and electrical resistivity (or impedance) sensors 244. Thermometer sensor 243 and electrical resistivity (or impedance) sensors 244 send data/measurements to the clinical device's processor 245.

The clinical device shown in FIG. 8 includes a display 246 in communication with the processor 245. The processor 245 is also in communication with a transmitter or transceiver 247. The transmitter or transceiver 247 is adapted to wirelessly send the data to the computerized device 204.

Computerized device 204 is shown having a computer processor 206. The processor is operable to retrieve from a memory or otherwise get the transmitted data, and to calculate various fertility related information, alerts, communications, and results. The processor may be programmed with a first or standalone software code 248 to compute various fertility related information and alerts. The add-on 249 used by third-party software, but is not needed for native software programs to communicate with the clinical device.

One embodiment of the present invention includes an alarm on the phone to facilitate and/or speed the receipt of data to the software. In embodiments, the fertility monitor software (using an app on a smart phone here as an example) is configured to interact with the phone's alarm or using local notifications to mimic the phone's alarm to aid in preparing the app to receive a signal from the clinical device and for convenience to the user.

By building the alarm to interact with the phone's alarm, the present invention allows the app to be launched by the phone's app so that it is ready to receive a signal from the clinical device.

Furthermore, in embodiments, the clinical device features a switch which turns off the phone's alarm. Examples of this switch may be a button, an accelerometer, a jiggle switch or a temperature or resistivity measurement threshold, which could trigger a system-wide notification for example. For added convenience, the app may also receive data from the clinical device without alarm by running the app in suspended mode or as a background service.

An example of the steps of this an embodiment is: An alarm on a fertility software (an app, for example) is to interact with the phone's alarm or using local notification mimic the phone's alarm. When (or before) the alarm is activated (namely, alarms), it may unlock the phone and launch the app to be ready to receive the signal from the clinical device. A switch on or signal from the clinical device shuts off the alarm on phone. The clinical device takes measurements and then sends the data (along with a time stamp) to the app on the phone In embodiments the system may be used to electronically trigger the release of, or recommend the use of in messages, contraceptive agents including drugs intended to disrupt ovulation or fertilization such as levonorgestrel depending on the user's fertility goals. Delivery includes, but is not limited, to peroral, transmucosal, cutaneous, subcutaneous, inhaled, or implanted means.

In embodiments the system may be used to electronically trigger the release of, or recommend the use of in messages, ovulation stimulants to increase chances of conception, such as gonadotropins depending on the user's fertility goals. Delivery includes, but is not limited, to peroral, transmucosal, cutaneous, subcutaneous, inhaled, or implanted means.

Additionally, in embodiments, the system may calculate the effectiveness of particular interventions on the user's fertility such as the use of acupuncture or yoga therapies using individual and/or aggregated data, by comparing a user's data to the data of a plurality of users using methods known to those skilled in the art of data mining.

In another variation of the invention an add-on or plug-in software 249 is integrated and run with a third-party software fertility application. For example, the add-on may provide for a tab or button available on the graphic user interface (GUI) of the third-party software allowing the user to sync or import the temperature and saliva data seamlessly and in the proper format and fields.

In another variation of the invention, a second or intermediary software programs the processor to modify and prepare the clinical data received from the clinical device 202 to seamlessly be accepted by another third-party software application. For example, this step may arrange and format the data into applicable fields for the third-party software. Another non-limiting example is to reorganize the data into a text file listing temperature and date separated by a comma or tab in sequence, or any other format which is importable into a third-party fertility software application The software described herein may take the form of an application for the iOS system used by devices such as the iPhone or iPad. However, it is contemplated that the software may be created for use by other operating systems (e.g., Windows, or Android) and devices (e.g., Droid smart phone, Dell laptop computer) and the invention is not to be limited to a particular format or programming language except where limited by the claims.

Computerized device 204 is shown having a display 208. The display may show various results and data determined by the processor. Examples include raw or processed data as well as results and alerts may be displayed.

Figure 9:
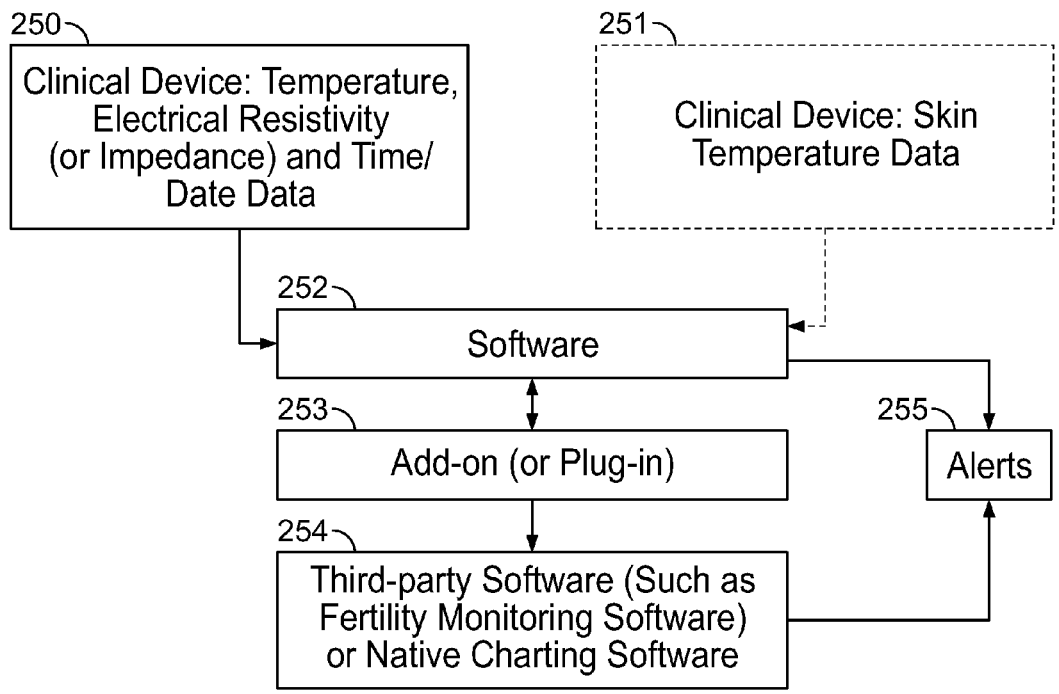

FIG. 9 is a flow chart illustrating a method to provide one or more fertility alerts to a user.

First, temperature data is obtained from a clinical device. In some embodiments data includes electrical resistivity measurements (250). Data may also include skin temperature data (251).

Step 252 states software. This step is directed to retrieving the data by a processor, and in particular by a processor operable or programmed with a first software to compute a fertility output or alert (255). Examples of output or alerts include without limitation a graphic of temperature versus time, a sound, vibration, communication, or light.

The method may also include a sync step to synchronize various data with third-party calendar programs such as, for example, Apple iCAL®, Microsoft Outlook®, etc. This step could be automatic, and enable synchronization of various data as described herein including but not limited to the user's period, and fertile window.

In yet another embodiment, alert information is sent to others designated by the user from the computerized device.

Step 253 states add-on (or plug-in). This step is directed to setting-up, or preparing the data for use by a third-party fertility software. This step may be carried out by a second or intermediary software adapted to modify and prepare the data for another third-party software application. For example, this step may arrange and format the data into applicable fields for the third-party software. Another non-limiting example is to reorganize the data into a text file listing temperature and date separated by a comma or tab in sequence, or any other format which is importable into a third-party fertility software application.

The add-on or plug-in software may be semi- or fully-integrated and run with a third-party software fertility application. For example, the add-on may enable a tab or button on the graphical user interface (GUI) of the third-party software allowing the user to sync or import the temperature and saliva data seamlessly and in the proper format and fields.

Step 254 states third-party software. This step involves syncing, importing or otherwise obtaining the data by the third-party software.

Step 255 states alerts, namely, to provide alerts, or otherwise inform or indicate to the users various fertility information such as, for example, a fever or fertility status. Alerts may be sent via SMS, email or other communication technologies using the typical protocols of these methods. In one embodiment alert information is sent to the user from the clinical device. In another embodiment, alert information is sent to the user from the computerized device.

In one embodiment, a programmed processor is operable to determine ovulation predictions for individual users by factoring in her age, cycle lengthen range, and observation of premenopausal symptoms by using on data from a plurality of cycle histories with artificial intelligence learning techniques and statistical modeling; and to guide the user through the process with reminders and recommendations.

Existing computerized fertility monitors, such as Persona or Clearblue Easy (both manufactured by Swiss Precision Diagnostics), have used predictive methods (also known as time-dependent regression methods, such as Cox's proportional Hazard Regression or a Time Series Analysis) solely based on measurements from an individual user's cycle, however because the regularity and length of the luteal and follicular phases, for example, changes throughout a woman's fertile years the repeatability of the length of the luteal or follicular phases of an individual's menstrual cycle is flawed.

Embodiments of the present invention include statistical modeling that account for the specific factors of age, cycle length variability, and the observance of perimenopausal or premenopausal signs in predicting ovulation. Examples of techniques include adaptive filters, influence diagrams, regression analysis, and Bayesian inference.

In one method, age, cycle length variability, and the observance of premenopausal signs are factored into the user's luteal phase. First, a regression is run on the luteal phase lengths to determine a predictive interval that captures the variability of the luteal phase lengths taken from data sets. This prediction interval is used to calculate the user's subsequent luteal phase length and for determining the level of confidence of that prediction. The prediction interval is dynamically updated with the recording of each cycle.

Preferable confidence levels of luteal phase length prediction interval (CLLPL) for individual users are shown in the table below:

|    | Age | Cycle length range | Premenopausal signs reported | LP length prediction interval | CLLPL |
|----|-----|---------------------|------------------------------|-------------------------------|-------|
| U1 | 22  | 27-30 days          | no                           | 12-14 days                    | 96%   |
| U2 | 31  | 28-30 days          | no                           | 13-15 days                    | 96%   |
| U3 | 38  | 28-29 days          | no                           | 13-14 days                    | 99%   |
| U4 | 44  | 20-22 days          | yes                          | 8-11 days                     | 90%   |

Another variation of the invention applies further statistical techniques to an indicator's past success in predicting the fertile window. Furthermore, through artificial intelligence techniques it may replace one sign for another, recommend other measurements to enhance accuracy, or query the user for input about additional fertility signs.

For example, the system may ask for cervical fluid evaluation input when needed to replace an irregular or atypical SER pattern. For example the invention fertility monitor may ask the user for a cervical fluid analysis only when needed, most likely limited to a couple days in a cycle, such as when the system fails to recognize a SER pattern and until ovulation is confirmed with the detection of a thermal shift.

Using artificial intelligence and learning techniques, the system can also make recommendations when to use the clinical device vaginally, such as when SER measurements are atypical or when to augment data to improve accuracy of ovulation prediction with other tests or measurements, such as FSH and luteinizing hormone tests.

For example, if the SER peak is not detected within a set parameter (e.g., SER peak time frame), say 8 days, a luteinizing hormone test or measurements might be suggested and the input results incorporated into the user's fertility profile.

The system may also analyze and indicate to the user when it is of no consequence to temporarily discontinue the use of the clinical device for some period of time, or when she may substitute the use of the clinical device with a skin temperature sensor. By comparing a user's cycle history to defined criteria, the system can determine if the regularity of a user's cycles allows her to use a skin sensor in lieu of the clinical device after the SER peak has been detected, and before the thermal shift.

Figure 10:
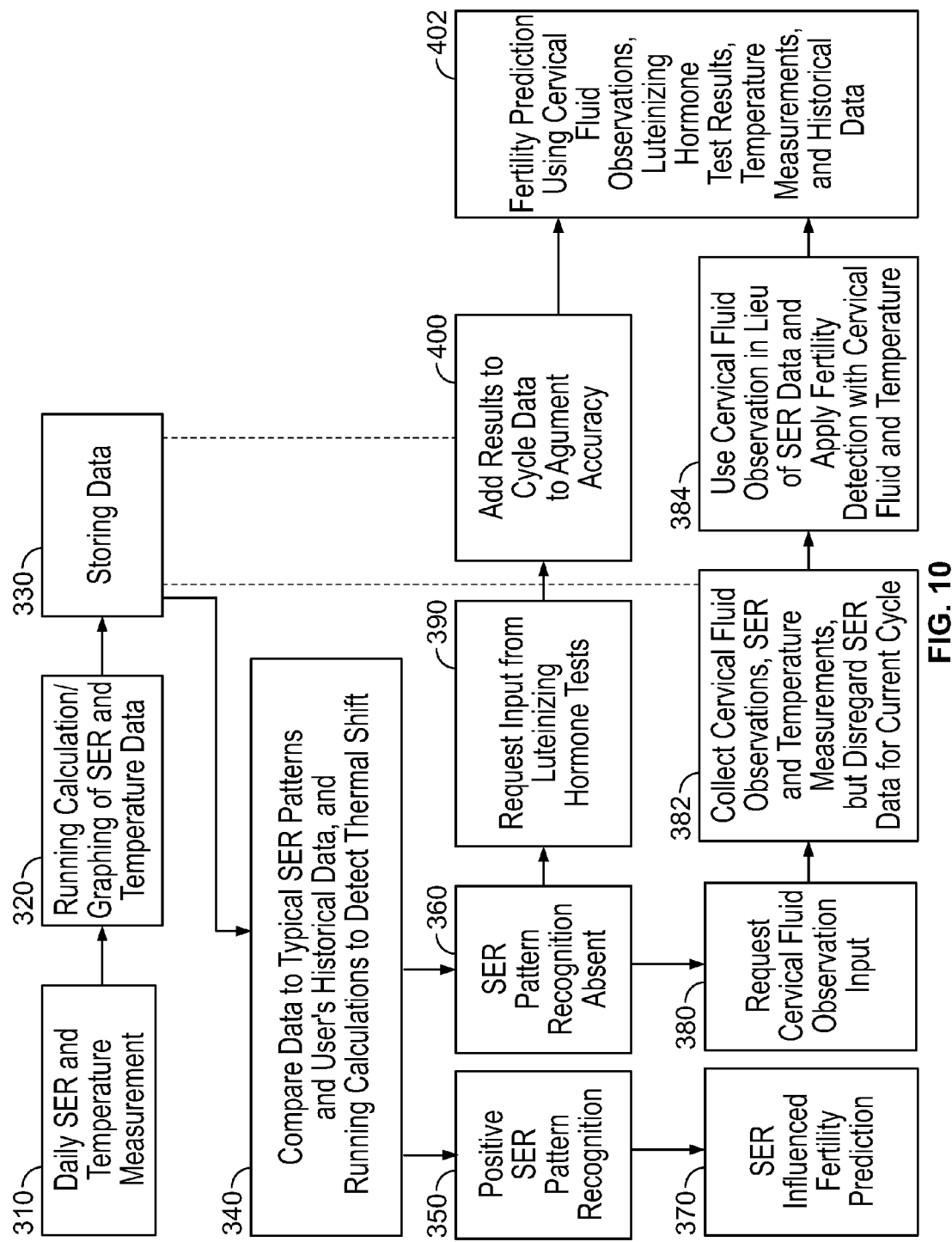
FIG. 10 is a flow chart illustrating a method to predict fertility.

FIG. 10 is another a flow chart illustrating a method 300 to indicate fertility based on additional inputs including cervical fluid observations and luteinizing hormone tests. First, step 310 states daily measurements are taken. Step 320 states a running calculation of data is made. Step 330, all data is stored. Step 340 calculations are run on data to detect patterns or predetermined thresholds. In step 350 for this example that also measures SER, a pattern is detected and fertility is subsequently determined (370) from this measurement. Or, as step 360 illustrates, when a SER pattern is absent the system requests (380) cervical fluid observations from the user. All the while she continues to use the clinical device (382), and use the cervical fluid observation results to override SER measurements for calculations to determine the user's fertility (384).

In parallel, the system may also request the results of a luteinizing hormone test (390) and incorporate the results (400) as additional data points in the user's cycle. Finally, step 402 states a predication of the user's fertility window is determined with the temperature measurements, the cervical fluid observations and the additional luteinizing hormone results.

Advantages

Various advantages arise from one or more of the embodiments described herein.

In an embodiment comprising a device that is portable, transmits information wirelessly, the device is operable to measure the electrical resistivity of saliva or cervical fluid and basal body temperature, so that the fertile window may be computed.

In another embodiment comprising a device having the ability to alarm or working with the alarm on a computerized device with which it is paired, the device can make it easier for a woman to remember to take her temperature by alerting and reminding her.

In another embodiment, the processor is operable to detect movement across time zones and daylight savings shifts and to automatically adjust measurements.

In another embodiment, raw and/or computed data is communicated directly into her (and those of whom she designates) electronic calendar on her computing device so that she may more easily monitor and communicate her fertility status.

In another embodiment comprising a design to prevent the insertion of the thermometer into a toddler's ear (such as an enlarged portion or audible alarm when moved improperly), the device can make it more resistant to and safer for handling by toddlers.

In another embodiment comprising a system as described herein, a woman's fertility history can be captured and analyzed for patterns, and predictions can be made about her future fertility. Furthermore, multiple inputs and sources can be integrated with the system creating a much richer data set for analysis.

In another embodiment comprising a system or method allowing the user to transmit the data, she can track her fertility more accurately and reliably.

In another embodiment comprising a system or method as described herein, the user can conveniently manage and share her fertility information and fertility status with others via SMS, email, phone calls or alarms, etc.

In another embodiment comprising a thermometer that transfers data to fertility tracking software, it is easier and less frustrating for women to monitor their fertility.

In another embodiment comprising software that automates fever tracking, a caregiver is assisted in recording a temperature's progression and is assisted in detecting patterns that bring concern drawing from fever thresholds based on age (or other variables), such as a fever spike, and alert the caregiver via SMS, email, phone calls or alarms. This may be especially useful for parents monitoring a sick child.

In another embodiment, a method starts tracking mid-cycle and provides feedback on the user's fertility based on multiple inputs.

In another embodiment, a method comprises analyzing inputs based on, but not limited to age, cycle patterns and length, in combination of basal body temperature and electrical resistivity measurements to determine fertility.

While the invention has been described in connection with particular embodiments, modifications of the apparatus and methods may become apparent to those skilled in the art. Accordingly, such modifications are to be included within the spirit and scope of the invention as defined in the following claims.

The invention claimed is:

1. An oral-based fertility monitoring system for insertion in the mouth and for monitoring fertility of a user, the system comprising:
   a clinical device, the clinical device comprising:
      a body adapted for comfortable insertion into the mouth of a patient;
      a first sensor located in the body, said first sensor adapted to measure temperature;
      a second sensor located in the body, the second sensor adapted to make a second measurement of the user; and
      a processor disposed within the body and being operable to receive a temperature signal and a second measurement signal from the temperature sensor and the second sensor respectively and to calculate a temperature value and a second measurement value of the user based on said received temperature signal and second measurement signal respectively; and
      said processor being further operable to determine a level of fertility based on at least said temperature value and said second measurement value.

2. The system of claim 1 further comprising a server, and wherein the server is operable to accept a first data of the user.

3. The system of claim 2 wherein the server further comprises a database, and the database having the first data stored thereon.

4. The system of claim 3 wherein the processor is operable to communicate with the server.

5. The system of claim 2 wherein the server is operable to receive a plurality of first data from a plurality of users and to store said plurality of first data on said database, thereby creating a set of aggregated data of multiple users.

6. The system of claim 5 where the processor is operable to compute a time estimate for the onset of menopause corresponding to the user based on data from a plurality of users and the first data of the user.

7. The system of claim 1 wherein the second sensor is a sensor for measuring at least one of the following: electrical resistivity, impedance, conductivity, electrolyte characteristics and hormones.

8. The system of claim 1 wherein the processor comprises an alarm.

9. The system of claim 1 further comprising at least one of following selected from the group consisting of a sound source, a light source, and a haptic technology.

10. The system of claim 9, further comprising a computerized device in communication with said clinical device, and wherein said computerized device is operable to provide at least one reward output indicative of the user's status, rate of completion of measurements, and the accuracy of her fertility predictions.

11. The system of claim 1 wherein the processor is operable to determine whether to request an ancillary input from the user.

12. The system of claim 11 wherein the ancillary input is a measurement selected from the group of a skin temperature, vaginal temperature, cervical fluid electrical resistivity, impedance, conductivity, electrolyte characteristics and hormone.

13. A fertility monitoring method comprising:
   receiving first data from a temperature sensor on a clinical device inserted into the mouth of the user;
   receiving second data from an ancillary sensor on the clinical device;
   receiving at least one user input;
   sending the first data and second data to a processor; and
   computing automatically on the processor a level of fertility based on the first data, the second data, and the at least one user input.

14. The method of claim 13 wherein the sending step comprises wirelessly transmitting data to a portable computing device.

15. The method of claim 13 further comprising requesting an ancillary input from the user; and using the ancillary input from the user to perform the computing step.

16. The system of claim 1 further comprising a transmitter, wherein the transmitter is configured to wirelessly send information from the clinical device.

17. The system of claim 16 further comprising a computerized device adapted to wirelessly receive information from the clinical device.

18. An oral-based fertility monitoring clinical device comprising:
- a body adapted for comfortable insertion into the mouth of a patient;
- a first sensor located in the body, said first sensor adapted to measure temperature;
- a second sensor located in the body, the second sensor adapted to make a second measurement of the user; and
- a processor disposed within the body and being operable to receive a temperature signal and a second measurement signal from the temperature sensor and the second sensor respectively and to calculate a temperature value and a second measurement value of the user based on said received temperature signal and second measurement signal respectively; and being further operable to determine a level of fertility based on at least said temperature value and said second measurement value.

19. The clinical device of claim 18 further comprising a transmitter, wherein the transmitter is configured to wirelessly send information from the clinical device.

20. The clinical device of claim 18 wherein the processor is operable to determine whether to request an ancillary input from the user.

\* \* \* \* \*